United States Patent
Sano et al.

(10) Patent No.: US 10,127,473 B2
(45) Date of Patent: Nov. 13, 2018

(54) DIAGNOSIS ASSISTING SYSTEM, DIAGNOSIS ASSISTING METHOD, AND PROGRAM THEREOF

(71) Applicant: NEC Corporation, Tokyo (JP)

(72) Inventors: Maki Sano, Tokyo (JP); Yoshiko Yoshihara, Tokyo (JP); Toru Sano, Tokyo (JP)

(73) Assignee: NEC Corporation, Tokyo (JP)

( * ) Notice: Subject to any disclaimer, the term of this patent is extended or adjusted under 35 U.S.C. 154(b) by 119 days.

(21) Appl. No.: 14/769,868

(22) PCT Filed: Feb. 24, 2014

(86) PCT No.: PCT/JP2014/000951
§ 371 (c)(1),
(2) Date: Aug. 24, 2015

(87) PCT Pub. No.: WO2014/132613
PCT Pub. Date: Sep. 4, 2014

(65) Prior Publication Data
US 2016/0004932 A1    Jan. 7, 2016

(30) Foreign Application Priority Data
Feb. 26, 2013    (JP) ................................. 2013-035788

(51) Int. Cl.
*G06T 7/00* (2017.01)
*G06K 9/00* (2006.01)
(Continued)

(52) U.S. Cl.
CPC ......... *G06K 9/6201* (2013.01); *G06F 19/321* (2013.01); *G06K 9/0014* (2013.01);
(Continued)

(58) Field of Classification Search
CPC ......... G06T 7/0012; G06T 2207/30024; G06T 2207/30096; G06T 7/0014; G06K 9/0014; G06F 19/26; G06F 19/321
See application file for complete search history.

(56) References Cited

U.S. PATENT DOCUMENTS

| | | | | |
|---|---|---|---|---|
| 5,134,662 A | * | 7/1992 | Bacus | G01N 15/1468 348/79 |
| 7,113,625 B2 | * | 9/2006 | Watson | G06F 19/321 382/128 |

(Continued)

FOREIGN PATENT DOCUMENTS

| | | |
|---|---|---|
| EP | 2333717 A1 | 6/2011 |
| EP | 2336969 A1 | 6/2011 |

(Continued)

OTHER PUBLICATIONS

International Search Report, Corresponding to PCT/JP2014/000951, dated Apr. 15, 2014, 2 pages.

*Primary Examiner* — Utpal Shah
(74) *Attorney, Agent, or Firm* — Wilmer Cutler Pickering Hale and Dorr LLP

(57) ABSTRACT

When making a diagnosis by synthetically taking into account the information obtained by preparing a plurality of samples using different staining methods or the like and sequentially observing the samples, a diagnostician must remember information about the plurality of samples.

The present invention includes image storage means for storing a reference image obtained by photographing a predetermined stained sample of and a comparison image obtained by photographing another stained sample of substantially identical biological tissues, partial image creation means for detecting a structure of the biological tissue from the reference image, cutting out from the comparison image a partial image that contains the structure detected, and (Continued)

storing into partial image storage means the partial image in association with the structure and the comparison image, image output means for outputting a result image that includes the reference image and the partial image, and the partial image storage means.

8 Claims, 10 Drawing Sheets

(51) Int. Cl.
G06K 9/62 (2006.01)
G06F 19/00 (2018.01)
G06K 9/46 (2006.01)
G06T 11/20 (2006.01)
G06T 7/73 (2017.01)

(52) U.S. Cl.
CPC ........... *G06K 9/00369* (2013.01); *G06K 9/46* (2013.01); *G06T 7/0014* (2013.01); *G06T 7/74* (2017.01); *G06T 11/20* (2013.01); *G06T 11/206* (2013.01); *G06T 2207/30024* (2013.01)

(56) References Cited

U.S. PATENT DOCUMENTS

| | | | |
|---|---|---|---|
| 2010/0054560 A1* | 3/2010 | Yamashita | A61B 5/055 382/128 |
| 2011/0128299 A1 | 6/2011 | Wakita et al. | |
| 2011/0131535 A1 | 6/2011 | Tagami et al. | |
| 2013/0071002 A1* | 3/2013 | Otsuka | G06T 7/0012 382/133 |
| 2013/0294676 A1* | 11/2013 | Parvin | A61B 5/0033 382/133 |

FOREIGN PATENT DOCUMENTS

| | | |
|---|---|---|
| EP | 2528034 A1 | 11/2012 |
| JP | 2007-244738 A | 9/2007 |
| JP | 2010-540906 A | 12/2010 |
| JP | 2011-002341 A | 1/2011 |
| JP | 2011-117991 A | 6/2011 |
| JP | 2011-118005 A | 6/2011 |
| WO | WO-2008/108059 A1 | 9/2008 |
| WO | WO-2011/89872 A1 | 7/2011 |

* cited by examiner

Fig.2

| IMAGE ID | IMAGE |
|---|---|
| PAS | PAS STAINED IMAGE 1 |
| IgG | IgG STAINED IMAGE 1 |
| IgA | IgA STAINED IMAGE 1 |
| IgM | IgM STAINED IMAGE 1 |
| C3c | C3 STAINED IMAGE 1 |
| ⋮ | |

REFERENCE IMAGE: PAS row

COMPARISON IMAGE: IgG, IgA, IgM, C3c rows and below

Columns labeled 11 (IMAGE ID) and 12 (IMAGE).

Fig.3

| STRUCTURE ID | IgG | IgA | IgM | C3c | ... |
|---|---|---|---|---|---|
| ① | PARTIAL IMAGE / FEATURE INFORMATION | ... | | | |
| ② | ... | | | | |
| ③ | | | | | |
| ... | | | | | |

Fig.7

| | IgG | IgA | IgM | C3c | C4c | C1q | Fibrinogen | Control |
|---|---|---|---|---|---|---|---|---|
| ① | ● (++) | ○ (-) | ◐ (±) | ○ (-) | ○ (-) | ○ (-) | ○ (-) | ○ (-) |
| ② | ● (+) | ○ (-) | ○ (-) | ○ (-) | ○ (-) | ○ (-) | ○ (-) | ○ (-) |
| ③ | ○ (-) | ○ (-) | ◐ (±) | ○ (-) | ○ (-) | ○ (-) | ○ (-) | ○ (-) |

CASE NO

PAS

INPUT COMMENT

EXPORT

CHECK HISTORY OF CHANGES

Report

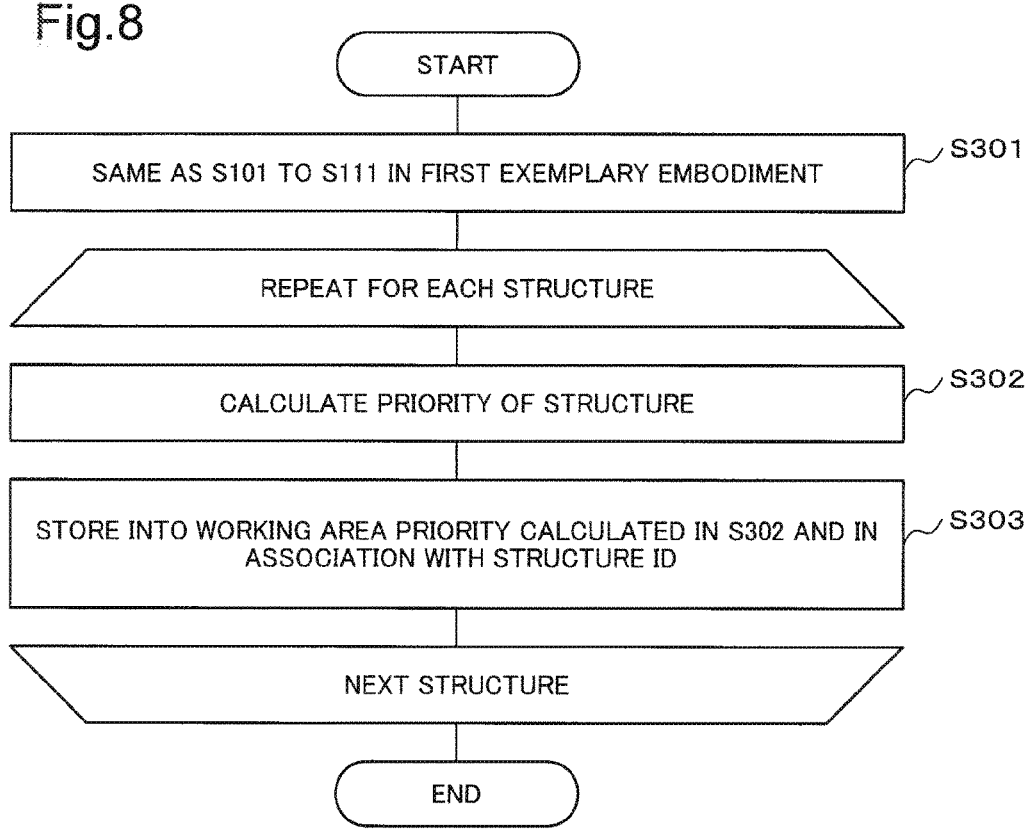
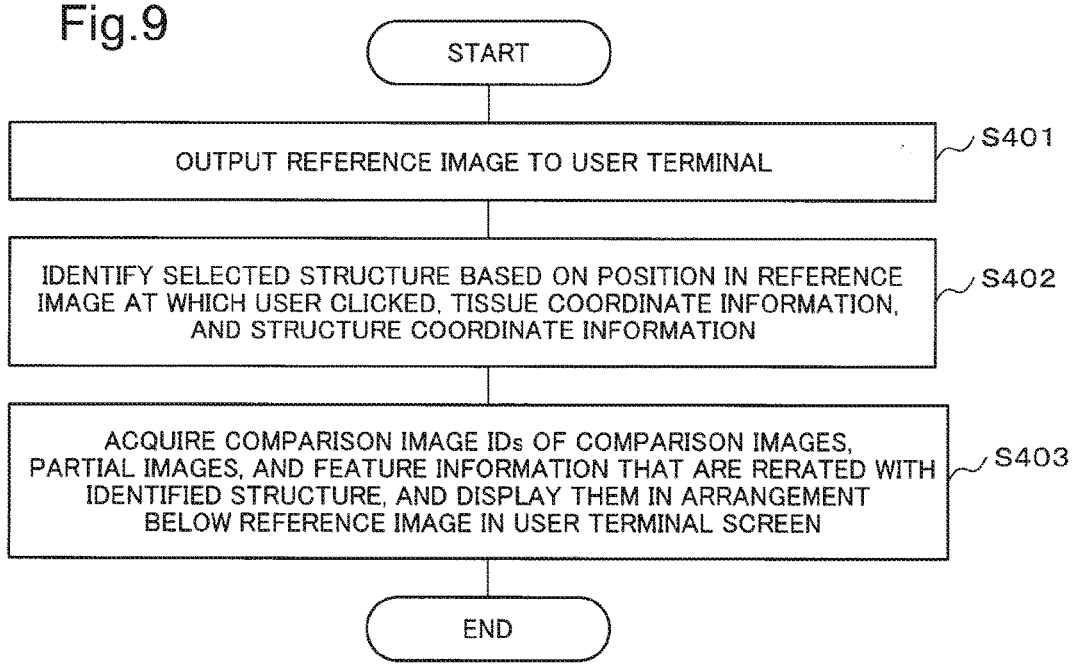

DIAGNOSIS ASSISTING SYSTEM, DIAGNOSIS ASSISTING METHOD, AND PROGRAM THEREOF

CROSS-REFERENCE TO RELATED APPLICATIONS

The present application is a national stage application of International Application No. PCT/JP2014/000951 entitled "Diagnosis Assisting System, Diagnosis Assisting Method, and Program For Same," filed on Feb. 24, 2014, which claims the benefit of priority from Japanese Patent Application No. JP2013-035788, filed on Feb. 26, 2013, the disclosures of which are incorporated herein in their entirety by reference thereto.

TECHNICAL FIELD

The present invention relates to a diagnosis assisting system, a diagnosis assisting method, and a program thereof in pathological diagnosis.

BACKGROUND ART

Pathological diagnoses using virtual slide images generated by scanning pathological samples through the use of virtual slide scanners are widespread. At the time of a pathological diagnosis, it sometimes becomes necessary to display a plurality of virtual slide images in an interlocked movement or display them in a superimposed manner on a viewer of a terminal.

As related technologies for displaying virtual slide images on viewers, there exists the following.

CITATION LIST

Patent Literature

[PTL 1] Japanese Unexamined Patent Application Publication No. 2007-244738
[PTL 2] Published Japanese Translation of PCT International Application Publication No. 2010-540906
[PTL 3] Japanese Unexamined Patent Application Publication No. 2011-002341
[PTL 4] Japanese Unexamined Patent Application Publication No. 2011-117991

PTL 1 describes that the whole image of an image and partial images thereof are displayed side by side in the same screen. The technology of this Literature, concretely, displays a whole image obtained by photographing a chest portion from the front and partial images in which marginal portions of asbestos shadows are made clear by enlarging the whole image, side by side in the same screen.

PTL 2 describes that a tissue specimen or an image is stained with a plurality of stains, for example, hematoxylin and the like.

PTL 3 describes that a region in which an extraction object structure appears is extracted from a virtual slide image of an object sample. The technology of this Literature, concretely, extracts a region in which an extraction object structure appears is extracted from a virtual slide image by using supervised training data recorded as feature information of the extraction object structure.

The cited Literature 4 describes that feature regions of a thumbnail image of an image obtained from a microscope can be discerned at a glance. According to the technology of this Literature, a pathologist can selectively skim only regions that affect a diagnosis while performing enlargement or reduction of their sizes, or the like.

SUMMARY OF INVENTION

Technical Problem

As for pathological diagnosis, it sometimes happens that a plurality of samples are prepared using serial sections of the same block (that is obtained by embedding in paraffin a tissue collected for diagnosis) by different staining methods and the like, and that information obtained after sequentially observing those samples is synthetically taken into account to make a diagnosis. In that case, there occurs a problem that during the period until making a diagnosis, a diagnostician has to remember information about a plurality of samples; thus, the burden on the diagnostician is great and the reviewing of samples frequently occurs.

However, none of the technologies describes in the foregoing Literatures can solve this problem. Therefore, an object of the present invention is to provide a diagnosis assisting system and diagnosis assisting method and program that solve the foregoing problem.

Solution to Problem

In order to achieve the object as in the above, the biological tissue display apparatus of the present invention includes: image storage means for storing a reference image obtained by photographing a prefixed stained sample and a comparison image obtained by photographing another stained sample, which are of substantially identical biological tissues; partial image creation means for detecting a structure of the biological tissue from the reference image, cutting out from the comparison image a partial image including the structure detected, and storing into partial image storage means the partial image in association with the structure and the comparison image; image output means for outputting the reference image and a result image that includes the partial image; and the partial image storage means.

Furthermore, the present invention provides a biological tissue image display method that includes; storing a reference image obtained by photographing a prefixed stained sample and a comparison image obtained by photographing another stained sample, which are of substantially identical biological tissues; detecting a structure of the biological tissue from the reference image, cutting out a partial image including the structure detected from the comparison image, storing the partial image in association with the structure and the comparison image; and outputting the reference image and a result image that includes the partial image.

Furthermore, the present invention provides a biological tissue image display program that causes a computer to execute: an image storage step of storing a reference image obtained by photographing a prefixed stained sample and a comparison image obtained by photographing another stained sample, which are of substantially identical biological tissues; a partial image creation step of detecting a structure of the biological tissue from the reference image, cutting out from the comparison image a partial image including the structure detected, and storing into partial image storage means the partial image in association with the structure and the comparison image; and an image output step of outputting the reference image and a result image that includes the partial image.

Advantageous Effects of Invention

The biological tissue display apparatus 100 of the present invention is able to lessen the burden on a diagnostician in a diagnosis using a plurality of different stained images.

BRIEF DESCRIPTION OF DRAWINGS

FIG. 2 is a diagram illustrating information stored in an image storage unit 10.

FIG. 3 is a diagram illustrating a configuration of a partial image storage unit 30.

FIG. 7 is a diagram illustrating an example of a display screen of the biological tissue display apparatus 100 according to a first exemplary embodiment.

FIG. 8 is a diagram illustrating an operation procedure of a partial image creation unit 20 according to a second exemplary embodiment.

FIG. 9 is a diagram illustrating an operation procedure of an image output unit 40 according to a third exemplary embodiment.

DESCRIPTION OF EMBODIMENTS

<First Exemplary Embodiment>

Hereinafter, exemplary embodiments of a biological tissue display apparatus 100 according to the present invention will be described with reference to the accompanying drawings. However, the configuration elements mentioned with the following exemplary embodiments are merely illustrative, and it is not intended to limit the technical scope of the present invention only to the configuration elements.

Figure 1:
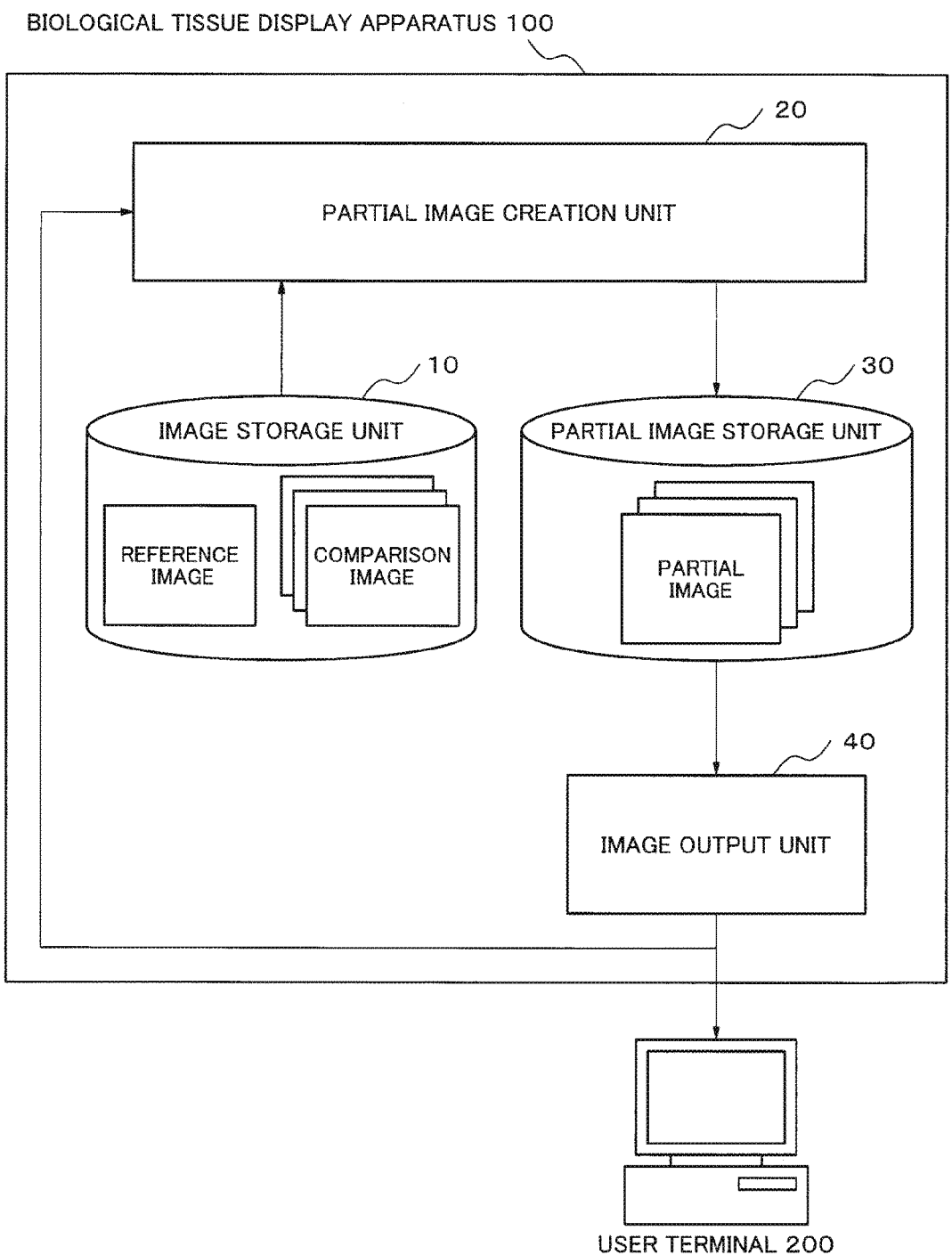
FIG. 1 is a diagram illustrating a configuration of a biological tissue image display apparatus 100.

FIG. 1 is a diagram illustrating a configuration of the biological tissue display apparatus 100 according to the present exemplary embodiment of the present invention. The biological tissue display apparatus 100 according to the present exemplary embodiment includes an image storage unit 10, a partial image creation unit 20, a partial image storage unit 30, and an image output unit 40. Furthermore, units with which the biological tissue display apparatus 100 of each of the exemplary embodiments are composed are implemented by hardware such as logic circuits. Furthermore, the units may be formed by a control unit of a computer, a memory device, a program loaded in the memory device, a storage unit that stores the program, such as a hard disk, and may be realized by various combinations of hardware and software. Unless otherwise stated, the realizing methods and apparatuses for the units are not limited. Incidentally, the image storage unit 10 and the partial image storage unit 30 may be a storage apparatus such as a disk. Furthermore, a user terminal 200 is connected to the biological tissue display apparatus 100.

The image storage unit 10 stores reference images obtained by photographing prefixed stained samples of biological tissues and comparison images obtained by photographing other stained samples thereof.

A reference image refers to an image with which a user recognizes a structure that the user desires to observe and by which the user specifies the structure to the biological tissue display apparatus 100, and refers to the image that is obtained by applying general staining or special staining to a biological tissue and photographing the biological tissue. The general staining is a staining method for generally recognizing various configuration elements that constitute biological tissues. Furthermore, the special staining is a staining method for selectively staining only a specific tissue component in a biological tissue.

The general staining and the special staining are, for example, hematoxylin eosin (H&E) staining, PAS (Periodic Acid Schiff) staining, PAM (Periodic Acid Methenamine) staining, Azan staining, EVG (Elastica-van Gieson) staining, Masson's trichrome staining, resorcin-fuchsin staining, orcein staining, silver staining, PTAH (phosphorus tungstic acid hematoxylin) staining, alcian blue staining, mucicarmine staining, and toluidine blue staining.

A comparison image is an image obtained by immunohistochemically staining and photographing a biological tissue. As for the immunohistochemical staining, there are, for example, a fluorescent antibody staining method and an enzyme antibody staining method.

The partial image creation unit 20 detects a structure of a biological tissue from a reference image acquired from the image storage unit 10, cuts out a partial image that includes the detected structure from a comparison image, and stores into the partial image storage unit 30 the partial image in association with the structure and the comparison image.

The image output unit 40 acquires from the partial image storage unit 30 the partial image 24 and the reference image relating to the partial image 24, and outputs a result image that include those images to the user terminal 200.

FIG. 2 is a diagram illustrating information stored in the image storage unit 10. The image storage unit 10 stores an image ID 11 (hereinafter, ID is an abbreviation of Identifier) that is identification information of an image and an image 12, which are in association with each other. The image ID 11 is, for example, PAS, which indicates a name of staining, in the case of a reference image, and IgG, IgA, or the like, which indicates a name of staining, in the case of a comparison image. Alternatively, the image ID 11 may be a file name, an extension, or the like regarding the image 12. Furthermore, as for the image 12, image data itself may be stored, or information that identifies the image data storage location, such as a file name or an URL (Uniform Resource Locator).

FIG. 3 is a diagram illustrating information that the partial image storage unit 30 stores. A structure ID 22 indicates identification information of a structure in a tissue. The structure is a portion that is used as an index for diagnosis and that exists in a tissue. The structure is a glomerulus, epidermal cells, a basement membrane, a dermal papilla, or the like. The comparison image ID 23 is identification information of a comparison image. In the present example, the comparison image ID 23 is an antibody name.

The partial image 24 is an image cut out from a comparison image in such a preset size as to include a structure. The partial image creation unit 20, for example, calculates the center of gravity of the structure and cuts out a partial image 24 so that the structure is at the center of the image. The feature information 25 is information that represents features, such as a shape or a state, of a structure detected from a reference image or a comparison image. The feature information 25 is the size, degree of circularity, staining intensity, staining pattern, or the like of the structure.

As FIG. 3 indicates, the partial image storage unit 30 stores a matrix formed by rows for structure IDs 22 and columns for comparison image IDs 23. The matrix stores, in a cell identified by a structure and a comparison image, a partial image 24 and feature information 25 acquired from the comparison image for the structure.

Figure 4A:
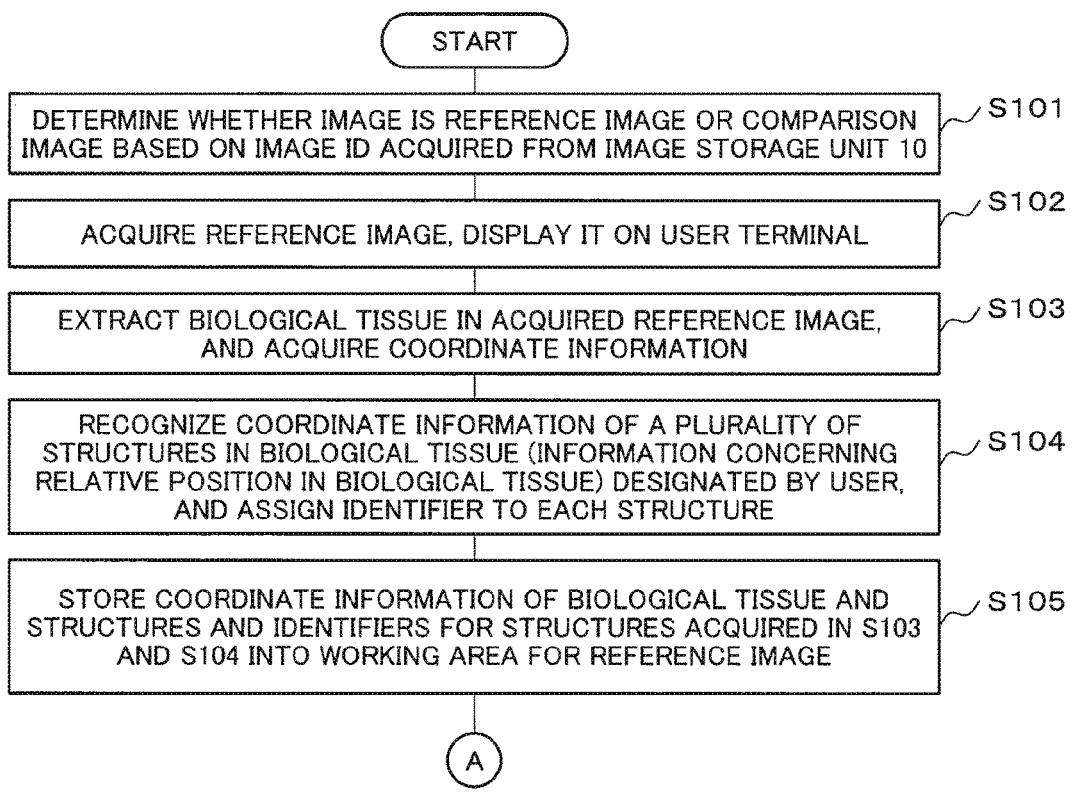
FIG. 4A is a diagram (part 1) illustrating an operation procedure of a partial image creation unit 20.
Figure 4B:
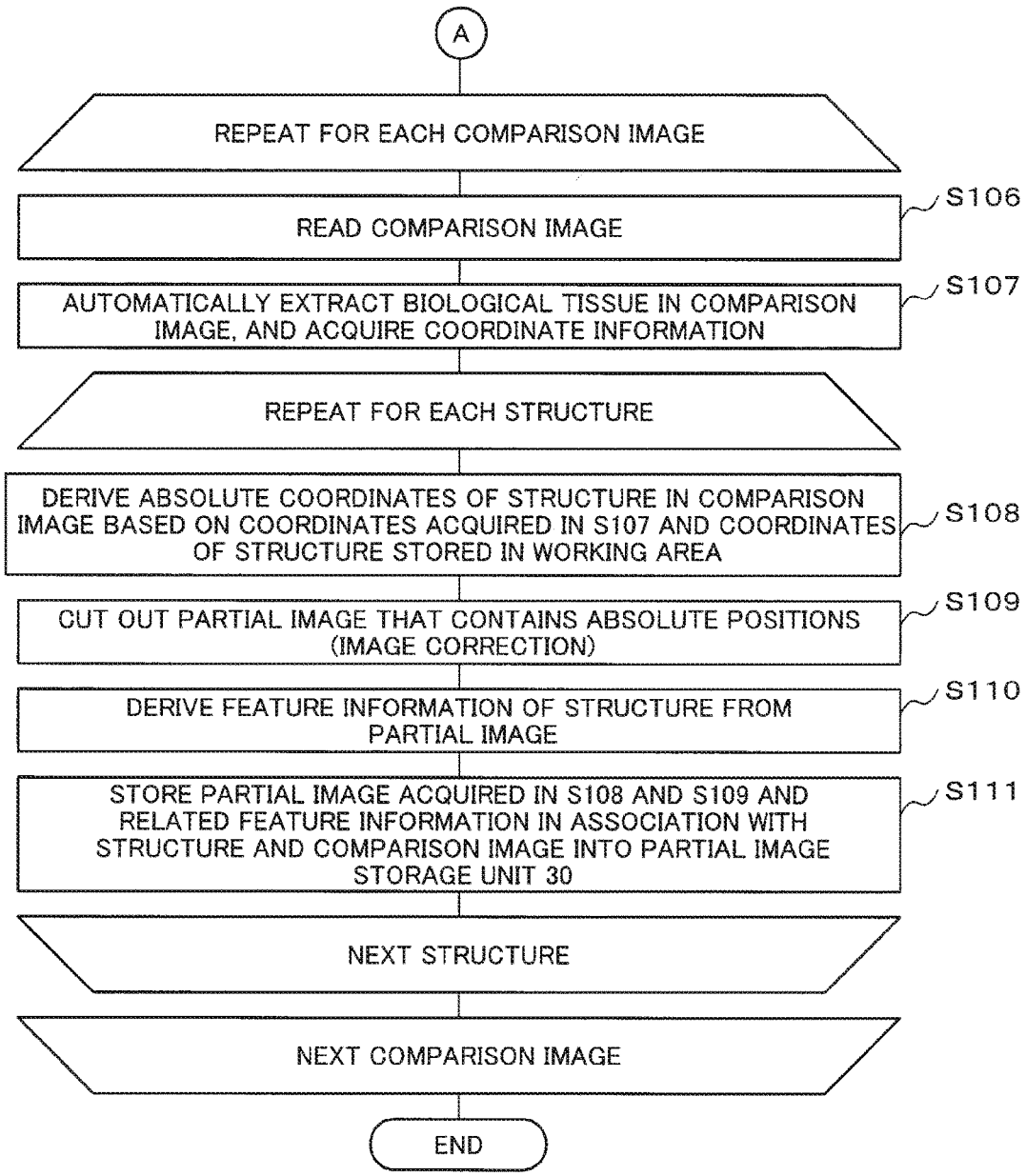
FIG. 4B is a diagram (part 2) illustrating the operation procedure of the partial image creation unit 20.

FIG. 4A and FIG. 4B are diagrams illustrating an operation procedure of the partial image creation unit 20 according to the present exemplary embodiment. The partial image creation unit 20, when activated by the user terminal 200, determines which of the images 12 is a reference image on the basis of the image IDs 11 stored in the image storage unit 10 (S101). The partial image creation unit 20, for example, acquires the image ID 11 of the reference image from the user terminal 200. The partial image creation unit 20 may determine the image 12 of an image ID 11 given beforehand as a reference image. The partial image creation unit 20, after acquiring the image 12 that is related with the image ID 11 of the reference image from the image storage unit 10, displays the reference image on the user terminal 200 (S102).

The partial image creation unit 20 extracts a biological tissue in the acquired reference image and acquires tissue coordinate information 21 of the biological tissue (S103). Note that the partial image creation unit 20 may carry out automatic extraction of a biological tissue by using an existing technology such as a technology described in Japanese Unexamined Patent Application Publication No. 9-96602. A user may designate a region of a biological tissue to the partial image creation unit 20 by using a mouse or the like of the user terminal 200.

Subsequently, the partial image creation unit 20 recognizes a plurality of pieces of structure coordinate information 26 concerning structures inside the biological tissue designated by the user (information concerning relative position in the biological tissue) and assigns a structure ID 22 (identification information about a structure) to each of the structures (S104).

Note that the partial image creation unit 20 detects a brightness difference and a color difference between a structure and other portions by using a known image processing technology and automatically recognizes the structures. The partial image creation unit 20 may use the technology of PTL 3. Alternatively, the user may designate a region of a structure to the partial image creation unit 20 by using a mouse or the like of the user terminal 200. Furthermore, the partial image creation unit 20 may automatically adopt a number as a structure ID 22, or the user may input a structure ID 22 from the user terminal 200.

Figure 5:
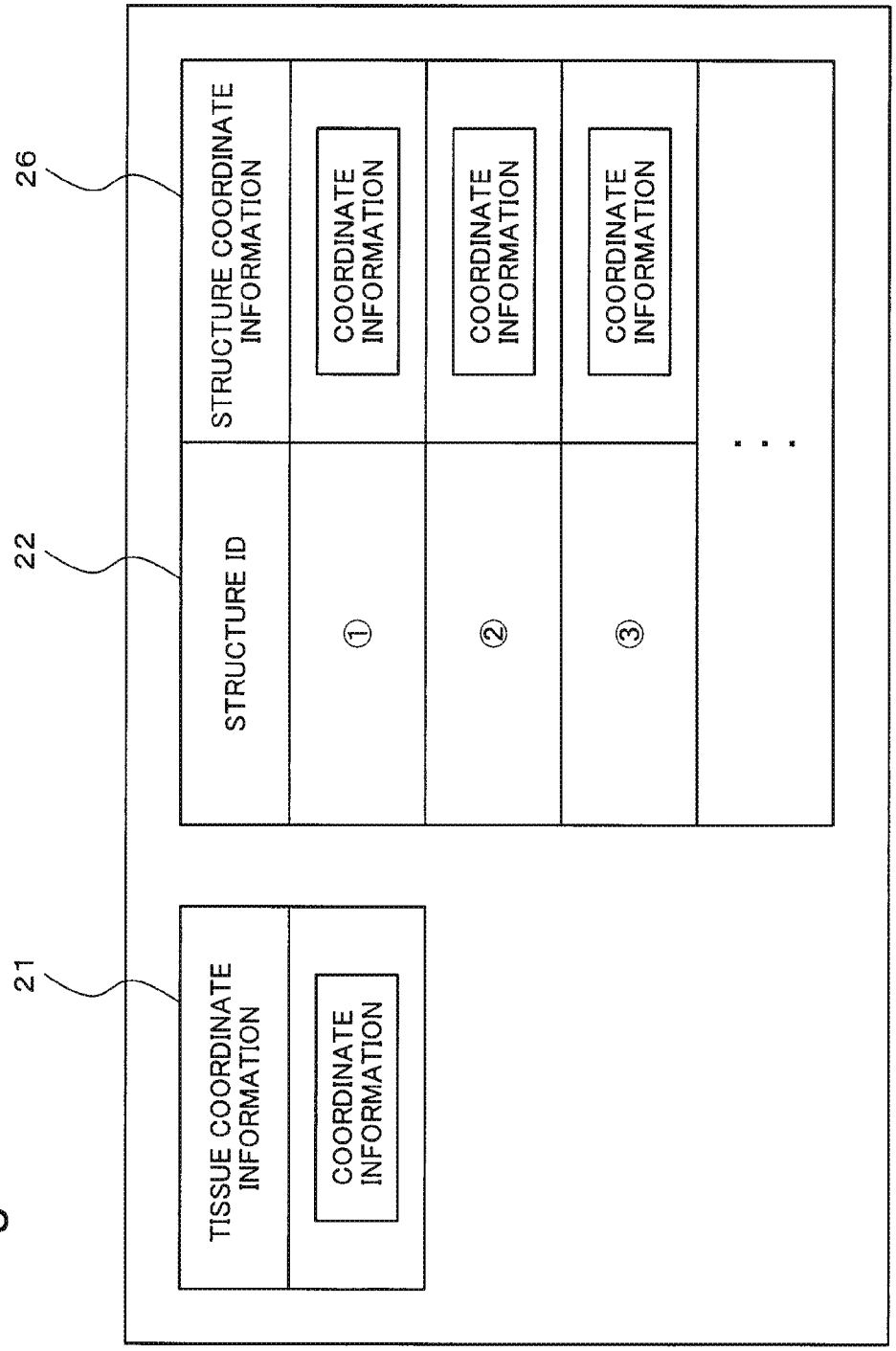
FIG. 5 is a diagram illustrating a working area that the partial image creation unit 20 creates.

After that, the partial image creation unit 20 stores the tissue coordinate information 21 and the structure coordinate information 26 and the structure ID 22 acquired in S103 and S104 into a working area in a memory (not illustrated) of the biological tissue display apparatus 100. FIG. 5 illustrates information stored in the working area. As illustrated, the structure IDs 22 and the structure coordinate information 26 are stored, which are related with each other, in the working area of the partial image creation unit 20 (S105). At this time, the partial image creation unit 20 stores the structure ID 22 in the partial image storage unit 30 as well.

Subsequently, the partial image creation unit 20 repeats S106 to S111 for each of the comparison images. The partial image creation unit 20 reads from the image storage unit 10 the image 12 of the comparison image from the image storage unit 10 and makes a copy of the image ID 11 as a comparison image ID 23 in the partial image storage unit 30 (S106). The partial image creation unit 20 automatically extracts a biological tissue in the comparison image and acquires tissue coordinate information 21 of the comparison image (S107). The automatic extraction of a biological tissue is substantially the same as in S103.

Subsequently, the partial image creation unit 20 repeats S108 to S111 for each of the structures stored in the working area. First, the partial image creation unit 20 derives absolute coordinate information of the structure in the comparison image from the tissue coordinate information 21 of the comparison image acquired in S107 and the structure coordinate information 26 stored in S105 (S108).

Furthermore, the partial image creation unit 20 cuts out a partial image 24 of a preset size so that the partial image 24 includes a position that the absolute coordinate of the structure indicate. Note that the preset size may be, for example, calculated from the screen size of the user terminal 200, the number of comparison images, and the like by the partial image creation unit 20, and may be given to the partial image creation unit 20 beforehand. Furthermore, the partial image creation unit 20, for example, finds the center of gravity of the structure and cuts out a partial image 24 such that the center of gravity is at the center of the partial image 24. Furthermore, the partial image creation unit 20 may perform correction of the brightness, contrast, color, and the like of the partial image 24 on the basis of a command of a user input from the user terminal 200 (S109).

The partial image creation unit 20 derives feature information 25 on the structure from the partial image 24 (S110). The feature information 25 is information representing the shape or state of the structure such as a detected edge, texture, or fluorescence intensity, the size, degree of circularity, or crowded degree (density) of the structure, the staining intensity, or the straining pattern. The partial image creation unit 20 derives the feature information 25 by using a known technology. For example, the partial image creation unit 20 derives a crowded degree (density) of the structure by obtaining color information of the structure and other portions by a color discriminant analysis and calculating a volume ratio therebetween.

Subsequently, the partial image creation unit 20 stores the partial image 24 acquired in S108 and S109 and the related feature information 25 in association with the structure and the comparison images into the partial image storage unit 30 (S111). According to above-described manner, the partial image storage unit 30 stores information as shown in FIG. 3. Incidentally, the partial image creation unit 20 may calculate feature information 25 from the reference image as well.

Figure 6:
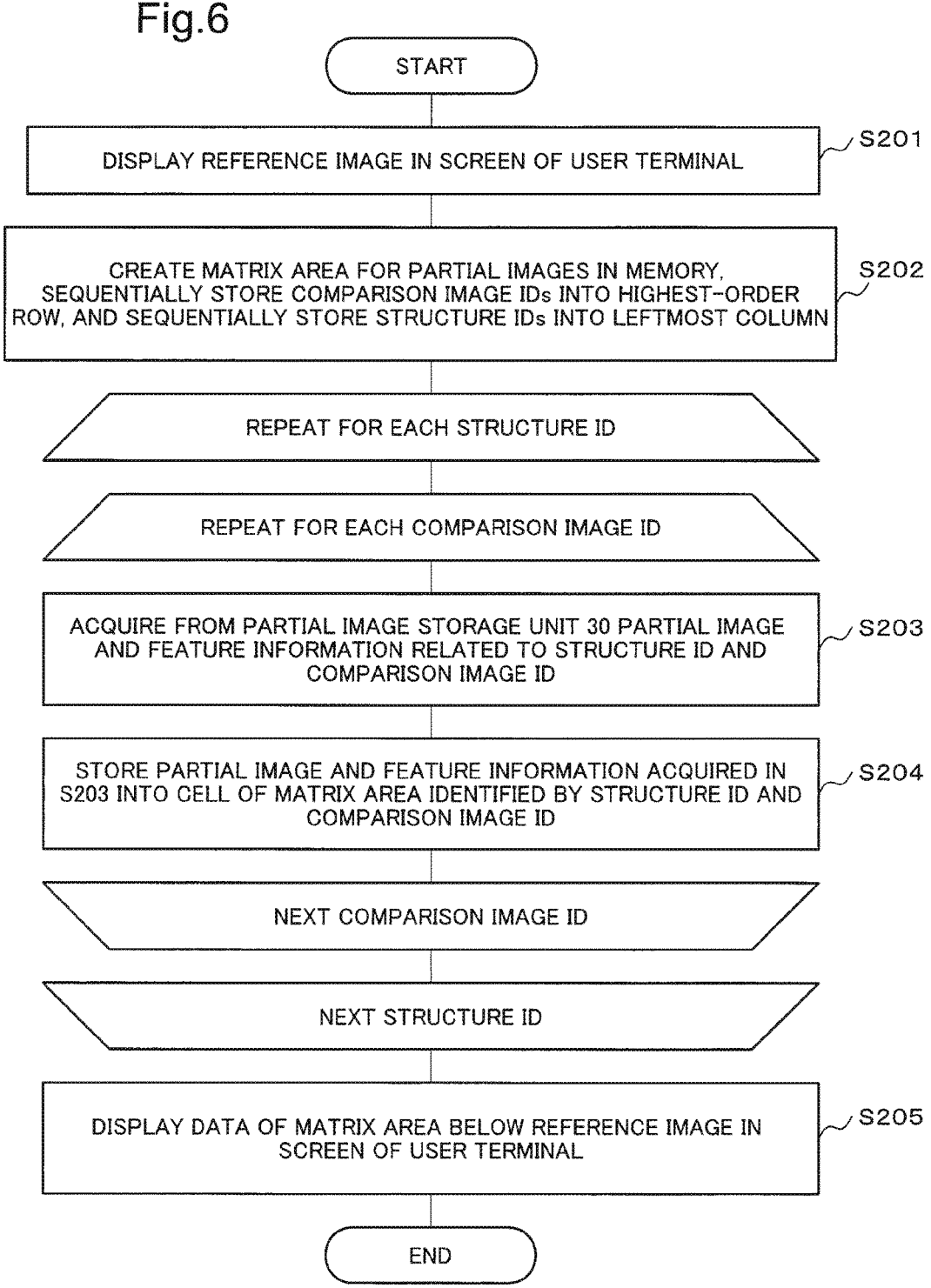
FIG. 6 is a diagram illustrating an operation procedure of an image output unit 40.

FIG. 6 is a diagram illustrating an operation procedure of an image output unit 40 according to the present exemplary embodiment. The image output unit 40 first displays a reference image in a screen of the user terminal 200 (S201). Next, the image output unit 40 creates a matrix area for partial images 24 in the memory, and sequentially stores comparison image IDs 23 acquired from the partial image storage unit 30 in the highest-order row, and sequentially stores structure IDs 22 in the leftmost column (S202).

Subsequently, the partial image output unit 40 repeats S203 to S204 for each of the comparison image IDs 23. Furthermore, the partial image output unit 40 acquires from the partial image storage unit 30 a partial image 24 and feature information 25 related to the structure ID 22 and the comparison image ID 23 (S203). The partial image output unit 40 stores the partial image 24 and the feature information 25 acquired in S203 into a cell in the matrix area identified by the structure ID 22 and the comparison image ID 23 (S204).

Finally, the partial image output unit 40 displays the data of the matrix area below the reference image in the screen of the user terminal 200 (S205).

FIG. 7 is a diagram illustrating an example of a result screen that the image output unit 40 according to the present exemplary embodiment outputs. In an upper portion of the result screen, a reference image and positions of detected structures are shown. In a lower portion there exists a matrix area identified by the structure IDs 22 and comparison image IDs 23, and in each cell there is displayed the related partial image 24 and at least a part of feature information 25.

The image output unit 40 may perform processing, such as enlargement, reduction, or move, on the reference image and the partial images 24 of a result screen in the screen, in response to an input apparatus such as a mouse. Furthermore, the image output unit 40 may likewise perform an image correction regarding the brightness of an image and the like.

For example, "++", "M", and the like, shown in FIG. 7, represent the staining intensity, staining pattern and the like of each of the structures, in the feature information 25. For example, "++" indicates that the fluorescence intensity of the structure is great, and "M" indicates the pattern of antibody deposition areas in the structure.

When the user gives a command to change the feature information 25 by a pull-down menu or a pop-up screen in a separate window during observation of a result screen, the image output unit 40 may, in response to the command, change the feature information 25 stored in the partial image storage unit 30.

Furthermore, when the user depresses an "INPUT COMMENT" button present in a right upper portion of the result screen during observation of the result screen, the image output unit 40 may, in response to that, acquire a comment from a keyboard or the like and add the comment to the feature information 25 stored in the partial image storage unit 30. When the user depresses an "EXPORT" button, the image output unit 40 may, in response to that, store the result screen under observation into an external storage apparatus, such as a USB (Universal Serial Bus) memory inserted into the user terminal 200.

Furthermore, when the user depresses a "Report" button, the image output unit 40 may, in response to that, create a report that includes the reference image, and a partial image 24 of a structure under observation and the feature information 25, and output the report to the user terminal 200.

The image output unit 40 may acquire and stores a history of enlargement, reduction and move of observation screens and of created reports into a disk apparatus or the like. In this case, when the user depresses a "CHECK HISTORY OF CHANGES" button, the image output unit 40 may, in response to that, output the history in the result screen.

The biological tissue display apparatus 100 according to the present exemplary embodiment is able to lessen the burden on an observer of a biological tissue. The reason is that the partial image creation unit 20 is able to detect structures of biological tissues from a reference image, to create partial images 24 that include the detected structures, and to display the reference image, the partial images 24, and the feature information 25 of the partial images 24 side by side.

<Second Exemplary Embodiment>

Subsequently, an operation procedure of a partial image creation unit 20 of a biological tissue display apparatus 100 according to the present exemplary embodiment will be described with reference to FIG. 8.

First, the partial image creation unit 20 performs substantially the same processing as in S101 to S111 of the first exemplary embodiment (S301). Subsequently, the partial image creation unit 20 repeats S302 to S303 for each of the structure IDs 22.

The partial image creation unit 20 calculates a priority of the structure (S302). The priority is a value that indicates the observation order of the structures. The partial image creation unit 20 calculates the priority, for example, by a weighted sum or the like using some pieces of the feature information 25 of the structure and related weighting values. The weighting values are preset for the individual features. As the presence or absence of a feature strongly affects estimation regarding malignancy of a biological tissue and the feature often appear in the comparison image from which the piece of feature information 25 is derived, the greater weighting value is set for the feature.

The feature information 25 used herein is, for example, the size, degree of circularity, staining intensity, and density of a structure. The partial image creation unit 20 may use only the feature information 25 derived from a specific comparison image or may also use feature information 25 derived from a plurality of comparison images. Furthermore, the partial image creation unit 20 may calculate a priority by using the feature information derived from a reference image.

Subsequently, the partial image creation unit 20 stores the priority calculated in S302 and the structure ID 22 in association with each other in the partial image storage unit 30 (S303).

The image output unit 40 of the present exemplary embodiment, when creating a matrix area for partial images 24 in a memory, sequentially stores comparison images IDs 23 in the highest-order row and sequentially stores structure IDs 22 in the order of priority in the leftmost column. Then, the image output unit 40 acquires from the partial image storage unit 30 partial image 24 and feature information 25 related to the structure ID 22 and the comparison image ID 23. The image output unit 40 stores the partial image 24 and the feature information 25 acquired into a cell, which is identified by the structure ID 22 and the comparison image ID 23, of the matrix area. Finally, the image output unit 40 displays data of the matrix area below the reference image in the screen of a user terminal.

The biological tissue display apparatus 100 according to the present exemplary embodiment is able to lessen the burden on an observer of a biological tissue. The reason is that the partial image creation unit 20 calculates a priority of each structure, on the basis of the feature information 25 about the structure, and displays the structures in the reference image displayed in a result screen and related partial images 24 in the order of priority. The observer can observe structures starting with a structure with high priority (important for the diagnosis).

<Third Exemplary Embodiment>

An operation procedure of a biological tissue display apparatus 100 according to the present exemplary embodiment will be described.

Incidentally, the operation procedure of the partial image creation unit 20 is substantially the same as in the first exemplary embodiment.

FIG. 9 is a diagram illustrating an operation procedure of an image output unit 40 according to the present exemplary embodiment. First, the image output unit 40 outputs a reference image to the user terminal 200 (S401). Next, the image output unit 40 identifies a selected structure on the basis of the position at which the user has clicked in the reference screen, and the tissue coordinate information 21 and the structure coordinate information 26 stored in the working area (S402). Furthermore, the image output unit 40 acquires the comparison image IDs 23 of the comparison images, and the partial images 24 and the feature information 25 that are related with the identified structure, and displays the acquired images and information side by side below the reference image in the screen of the user terminal 200 (S403).

Figure 10:
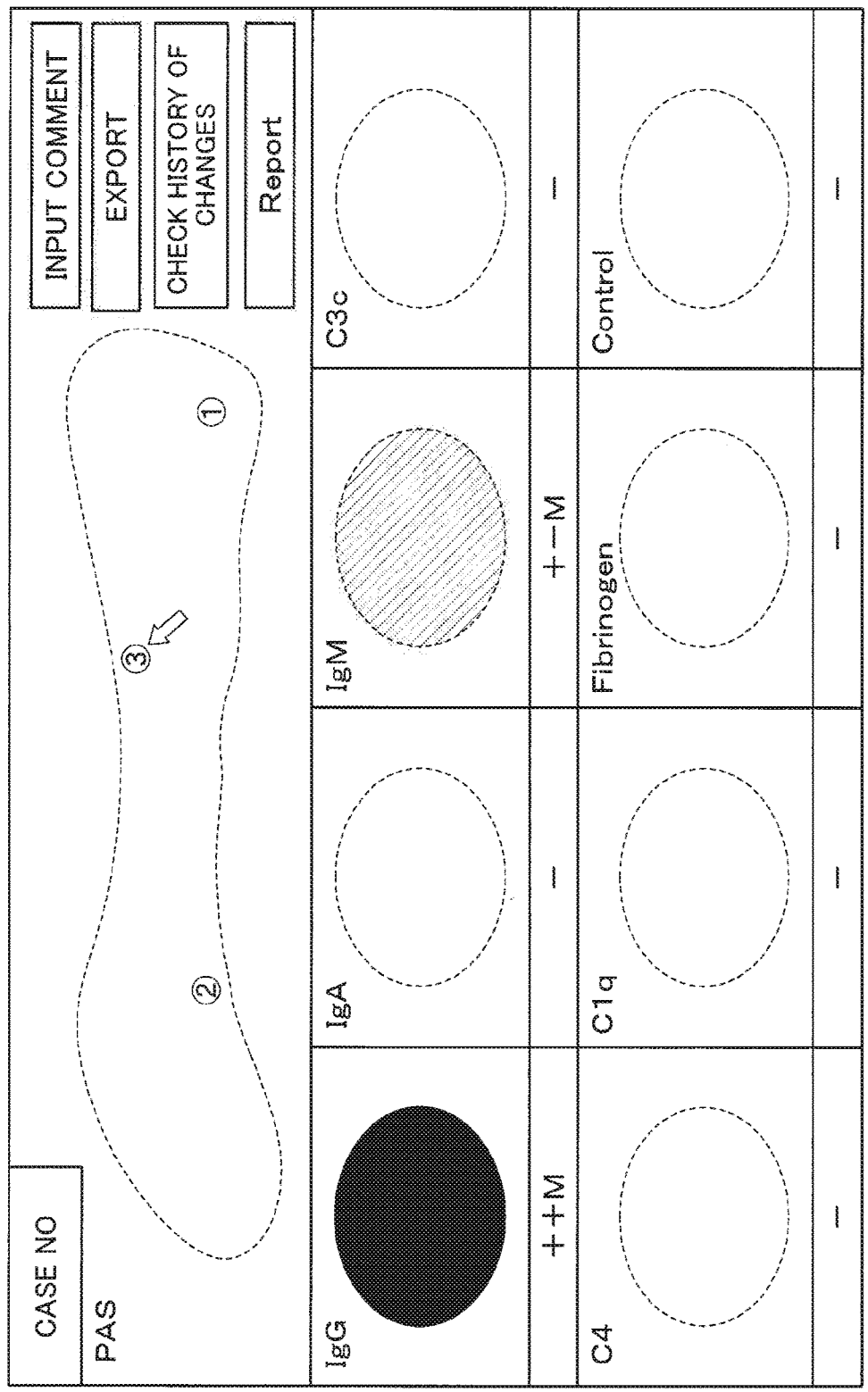
FIG. 10 is a diagram illustrating an example of a display screen of a biological tissue display apparatus 100 according to the third exemplary embodiment.

FIG. 10 is a diagram illustrating an example of a result screen that the image output unit 40 according to the present exemplary embodiment outputs. In an upper portion of the result screen, there are displayed a reference image and structures. Furthermore, a lower portion of the result screen is formed by a matrix area including a plurality of cells. In each of the cells, a partial image 24 that is associated with a comparison image ID 23 and feature information 25 are simultaneously displayed. Although the present diagram illustrates a matrix area formed by pluralities of rows and columns, the number of rows or columns constituting the matrix is not limited to a plural number but may be at least one.

Various functions of the image output unit 40, such as an "INPUT COMMENT" and an "EXPORT", are substantially the same as in the first exemplary embodiment, and therefore descriptions thereof are omitted herein.

The biological tissue display apparatus 100 according to the present exemplary embodiment is able to lessen the burden on an observer of a biological tissue. The reason is that the image output unit 40, when recognizing the position in a screen designated by the observer, identifies the selected structure on the basis of the position, the tissue coordinate information 21, and the structure coordinate information. Furthermore, the image output unit 40 acquires the comparison image IDs 23 of the comparison images, the partial images 24, and the feature information 25 that is associated with the identified structure, and displays the images and information side by side below the reference image in the screen of the user terminal 200. As a result, the observer can easily see the partial image 24 and the feature information of the designated structure.

<Fourth Exemplary Embodiment>

A biological tissue display apparatus 100 according to the present exemplary embodiment includes an image storage unit 10, a partial image creation unit 20, a partial image storage unit 30, and an image output unit 40. The image storage unit 10 stores a reference image obtained by photographing a predetermined stained sample and comparison images obtained by photographing other stained samples, which are of substantially identical biological tissues. The partial image creation unit 20 detects structures of the biological tissue from the reference image, cuts out, from the comparison images, partial images 24 including the structures detected, and stores the partial images 24 into the partial image storage unit 30 in association with the structures and the comparison images. The image output unit 40 outputs a result image that includes the reference image and the partial images 24.

The biological tissue display apparatus 100 according to the present exemplary embodiment is able to lessen the burden on an observer in a diagnosis that uses a plurality of different stained images. For example, in a fluorescent antibody method test in a kidney biopsy, an observer needs to observe features of all the glomeruli present in the tissue in each of a plurality of different stained images (the presence or absence of a glomerulus that is positive, the positive pattern, and the fluorescence intensity). When there are many glomeruli that are observation objects, this observation is an operation that causes a great burden on an observer. In the biological tissue display apparatus 100 according to the present exemplary embodiment, the partial image creation unit 20 detects glomeruli or the like from a reference image, generates partial images 24 that include detected glomeruli or the like, and displays the reference image and the partial images 24 side by side, so that the burden on the observer lessens.

While the invention of the present application has been described above with reference to the exemplary embodiments (and examples), the invention of the present application is not limited to the foregoing exemplary embodiments (and examples). The configurations and details of the invention of the present application can be changed in various manners that a person skilled in the art can understand within the scope of the invention of the present application.

This application claims the priority based on Japanese Patent application No. 2013-035788 filed on Feb. 26, 2013, the disclosure of which is incorporated herein in its entirety.

REFERENCE SIGNS LIST

10 Image storage unit
11 Image ID
12 Image
20 Partial image creation unit
21 Tissue coordinate information
22 Structure ID
23 Comparison image ID
24 Partial image
25 Feature information
30 Partial image storage unit
40 Image output unit
100 Biological tissue display apparatus
200 User terminal

The invention claimed is:

1. A biological tissue image display apparatus comprising:
memory storing instructions; and
one or more processors to execute the instructions to:
store a reference image obtained by photographing a prefixed stained sample and a comparison image obtained by photographing another stained sample, which are of substantially identical biological tissues;
detect a structure of the biological tissue from the reference image;
generate a partial image as an independent image by cutting out a portion from the comparison image that includes the structure detected;
store the partial image in association with the structure and the comparison image;
output a result screen that includes the reference image and the partial image;
store a plurality of comparison images each corresponding to the comparison image;
detect a plurality of structures each corresponding to the structure from the reference image, cut out from the plurality of comparison images partial images each corresponding to the partial image including one of the plurality of structures detected, and store the partial images each being in association with the structure and the comparison image; and
create a matrix in which identification information of the plurality of structures is arranged along a first axis of the result screen and in which identification information of the plurality of comparison images is arranged along a second axis of the result screen, and arrange the partial images in cells of the matrix in such a way that the partial images including same structures are arranged in the cells whose distances from the second axis are same and the partial images cut out from a same comparison image are arranged in the cells whose distances from the first axis are same, the cells being identified by the structures and the comparison images that are in association with the partial images.

2. The biological tissue image display apparatus according to claim 1, the one or more processors to execute the instructions to:
 extract feature information of each of the plurality of structures from the reference image and the partial images, determine priorities indicating an observation order of the plurality of structures on a basis of the feature information extracted, and store the priorities in association with the plurality of structures, and
 arrange the identification information of the plurality of structures along the first axis in order of the priorities.

3. The biological tissue image display apparatus according to claim 1, the one or more processors to execute the instructions to:
 display the reference image, receive selection information of at least one of the plurality of structures, arrange identification information of the plurality of comparison images along a preset axis of the result screen, acquire from the partial image storage means the partial images in association with the structures selected, and arrange the partial images in cells near the identification information of the plurality of comparison images.

4. The biological tissue image display apparatus according to claim 1, the one or more processors to execute the instructions to:
 extract, from each of the plurality of partial images, feature information of each of the structures included in the partial image, and store the feature information in association with the partial image, and
 arrange the partial images and the feature information associated with the partial images together in the cells.

5. A biological tissue image display method comprising:
 storing a reference image obtained by photographing a prefixed stained sample and a comparison image obtained by photographing another stained sample, which are of substantially identical biological tissues;
 detecting a structure of the biological tissue from the reference image
 generating a partial image as an independent image by cutting out a portion from the comparison image that includes the structure detected;
 storing the partial image in association with the structure and the comparison image;
 outputting a result screen that includes the reference image and the partial image;
 storing a plurality of comparison images each corresponding to the comparison image;
 detecting a plurality of structures each corresponding to the structure from the reference image, cutting out from the plurality of comparison images partial images each corresponding to the partial image including one of the plurality of structures detected, and storing the partial images each being in association with the structure and the comparison image; and
 creating a matrix in which identification information of the plurality of structures is arranged along a first axis of the result screen and in which identification information of the plurality of comparison images is arranged along a second axis of the result screen, and arranging the partial images in cells of the matrix in such a way that the partial images including same structures are arranged in the cells whose distances from the second axis are same and the partial images cut out from a same comparison image are arranged in the cells whose distances from the first axis are same, the cells being identified by the structures and the comparison images that are in association with the partial images.

6. The biological tissue image display method according to claim 5, comprising:
 extracting feature information of each of the plurality of structures from the reference image and the partial images, determining priorities indicating an observation order of the plurality of structures on a basis of the feature information extracted, and storing the priorities in association with the plurality of structures; and
 arranging the identification information of the plurality of structures along the first axis in order of the priorities.

7. The biological tissue image display method according to claim 5, comprising:
 displaying the reference image, receiving selection information of at least one of the plurality of structures, arranging identification information of the plurality of comparison images along a preset axis of the result screen, acquiring the partial images associated with the structures selected, and arranging the partial images in cells near the identification information of the plurality of comparison images.

8. A non-transitory computer readable medium storing a biological tissue image display program causing a computer to execute:
 an image storage step of storing a reference image obtained by photographing a prefixed stained sample and a comparison image obtained by photographing another stained sample, which are of substantially identical biological tissues;
 a partial image creation step of:
  detecting a structure of the biological tissue from the reference image,
  generating a partial image as an independent image by cutting out a portion from the comparison image that includes the structure detected, and
  storing into a partial image storage unit the partial image in association with the structure and the comparison image; and
 an image output step of:
  outputting a result screen that includes the reference image and the partial image;
  storing a plurality of comparison images each corresponding to the comparison image;
  detecting a plurality of structures each corresponding to the structure from the reference image, cutting out from the plurality of comparison images partial images each corresponding to the partial image including one of the plurality of structures detected, and storing the partial images each being in association with the structure and the comparison image; and
  creating a matrix in which identification information of the plurality of structures is arranged along a first axis of the result screen and in which identification information of the plurality of comparison images is arranged along a second axis of the result screen, and arranging the partial images in cells of the matrix in such a way that the partial images including same structures are arranged in the cells whose distances from the second axis are same and the partial images cut out from a same comparison image are arranged in the cells whose distances from the first axis are same, the cells being identified by the structures and the comparison images that are in association with the partial images.

* * * * *